United States Patent [19]

Minagawa et al.

[11] Patent Number: 4,525,506
[45] Date of Patent: Jun. 25, 1985

[54] POLYHYDRIC ALCOHOL ETHERS OF 2,2,6,6-TETRAMETHYL-4-PIPERIDONE KETALS AND SYNTHETIC RESIN COMPOSITIONS

[75] Inventors: Motonobu Minagawa, Koshigaya; Naohiro Kubota, Ageo; Toshihiro Shibata, Omiya; Ryozo Arata, Urawa, all of Japan

[73] Assignee: Adeka Argus Chemical Co., Ltd., Urawa, Japan

[21] Appl. No.: 478,610

[22] Filed: Mar. 25, 1983

[30] Foreign Application Priority Data

Mar. 31, 1982 [JP] Japan .................................. 57-53270

[51] Int. Cl.³ .............................................. C08K 5/34
[52] U.S. Cl. .............................. 524/102; 546/19
[58] Field of Search ......................... 524/102; 546/19

[56] References Cited

U.S. PATENT DOCUMENTS

| | | | |
|---|---|---|---|
| 3,126,393 | 3/1964 | Young | 546/248 |
| 3,899,464 | 4/1984 | Murayama et al. | 524/95 |
| 4,105,626 | 8/1978 | Brunetti et al. | 524/102 |
| 4,125,533 | 11/1978 | Murayama et al. | 524/102 |
| 4,128,608 | 12/1978 | Minagawa et al. | 524/102 |
| 4,222,931 | 9/1980 | Minagawa et al. | 524/102 |
| 4,323,684 | 4/1982 | Kubota et al. | 546/19 |

*Primary Examiner*—John Kight
*Assistant Examiner*—Kriellion Morgan

[57] ABSTRACT

Polyhydric alcohol ethers of 2,2,6,6-tetramethyl-4-piperidone ketals are provided, having the formula:

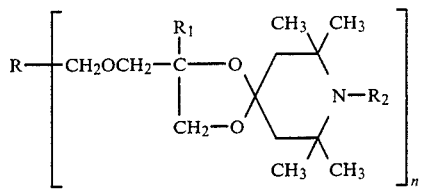

wherein:
R is selected from the group consisting of hydrogen, alkyl having from one to about eight carbon atoms, and alkyleneoxyalkylene, each alkylene having from two to about eight carbon atoms;
$R_1$ is selected from the group consisting of hydrogen and alkyl having from one to about four carbon atoms;
$R_2$ is selected from the group consisting of hydrogen; oxyl O; alkyl, hydroxy alkyl and epoxyalkyl having from one to about eighteen carbon atoms; acyl having from one to about eighteen carbon atoms; cycloalkyl having from three to about eighteen carbon atoms; phenyl; phenalkyl and alkylphenyl having from seven to about twenty-four carbon atoms; and
n is a number from 3 to 6 as well as synthetic resin compositions having an improved resistance to deterioration and containing such compounds.

26 Claims, No Drawings

POLYHYDRIC ALCOHOL ETHERS OF 2,2,6,6-TETRAMETHYL-4-PIPERIDONE KETALS AND SYNTHETIC RESIN COMPOSITIONS

Polymers such as polyethylene, polypropylene, ABS resin, polyvinyl chloride and polyurethane undergo degradation and discoloration when subjected to irradiation by ultraviolet light such as sunlight, with deterioration in mechanical strength. Accordingly, various kinds of light stabilizers have been incorporated in such polymers to lessen their deterioration. However, the available stabilizers are unsatisfactory in their stabilizing effectiveness, unstable to heat and oxidation, and soluble in water or organic solvents. Some stabilizers even impart a color of their own to the polymers.

2,2,6,6-tetramethyl piperidine compounds do not impart color to the polymer, and act as quenchers. Many piperidine compounds, therefore, are proposed as light stabilizers.

Murayama et al U.S. Pat. No. 4,212,974, patented July 15, 1980, provides piperidine derivatives having the formula:

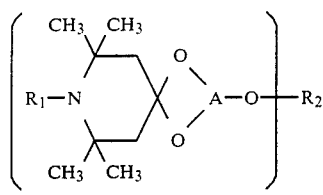

wherein $R_1$ represents hydrogen, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, n is an integer of 1 to 4; when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, a N-substituted carbamoyl group, a N-substituted thiocarbamoyl group, a monovalent group from an oxoacid or group

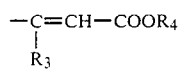

in which $R_3$ represents hydrogen atom, a lower alkyl group or phenyl group and $R_4$ represents an alkyl group; when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid; when n is 3, $R_2$ represents an aromatic triacyl group or a trivalent group from an oxoacid; and when n is 4, $R_2$ represents an aromatic tetraacyl group, and A represents a group

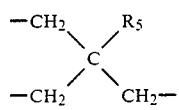

in which $R_5$ represents hydrogen atom or a lower alkyl group, or, when n is 1, $R_5$ may represent together with $R_2$ a group

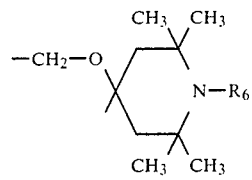

in which $R_6$ represents the same group as defined in $R_1$ and may be the same or different from $R_1$, or a group

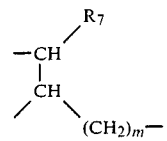

in which n is 1 or 2 and $R_7$ represents hydrogen atom or, when n and m are 1, $R_7$ represents methylene group together with $R_2$.

These piperidine derivatives have a stabilizing effect against photo- and thermal-deterioration of synthetic polymeric materials such as polyolefin; polyvinyl chloride, polyvinylidene chloride, polyacetal, polyester, polyamide, polyurethane, epoxy resins and the like.

The known piperidine compounds are also unsatisfactory in their stabilizing effectiveness, are volatile and lost from the polymer at high temperatures and are extracted by water.

In accordance with the present invention, polyhydric alcohol ethers of 2,2,6,6-tetramethyl-4-piperidone ketals are provided, having the formula:

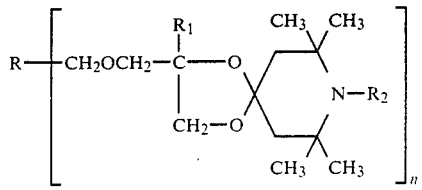

wherein:
R is selected from the group consisting of hydrogen, alkyl having from one to about eight carbon atoms, and alkyleneoxyalkylene, each alkylene having from two to about eight carbon atoms;
$R_1$ is selected from the group consisting of hydrogen and alkyl having from one to about four carbon atoms;
$R_2$ is selected from the group consisting of hydrogen; oxyl O; alkyl, hydroxy alkyl and epoxyalkyl having from one to about eighteen carbon atoms; acyl having from one to about eighteen carbon atoms; cycloalkyl having from three to about eighteen carbon atoms; phenyl; phenalkyl and alkylphenyl having from seven to about twenty-four carbon atoms; and n is a number from 3 to 6;

as well as synthetic resin compositions having an improved resistance to deterioration and containing such compounds.

Exemplary R and $R_2$ alkyl are methyl, ethyl, propyl, isopropyl, butyl, isobutyl, tert-butyl, sec-butyl, amyl, isoamyl, tert amyl, hexyl, heptyl, octyl, isooctyl, 2-ethylhexyl, nonyl, isononyl, decyl, undecyl, dodecyl, palmityl, myristyl and stearyl.

Exemplary $R_2$ cycloalkyl include cyclopropyl, cyclobutyl, cyclopentyl, cyclohexyl, cycloheptyl and cyclooctyl.

Exemplary $R_2$ phenalkyl and alkyl phenyl include benzyl, phenethyl, phenbutyl, phenhexyl, tolyl, xylyl, mesityl, butylphenyl, octylphenyl, nonylphenyl and dodecylphenyl.

Exemplary $R_2$ hydroxyalkyl include 2-hydroxyethyl, 2-hydroxypropyl and 2-hydroxybutyl; and $R_2$ epoxyalkyl include 2,3-epoxypropyl, 2,3-epoxybutyl, 1,2-epoxybutyl and 1,2-epoxyamyl.

Exemplary $R_2$ acyl are acetyl, propionyl, butyroyl, octanoyl, lauroyl, stearoyl, palmitoyl and myristoyl.

Exemplary $R_1$ alkyl are methyl, ethyl, propyl, isopropyl, butyl, isobutyl and tert-butyl.

Exemplary R alkyleneoxyalkylene include ethyleneoxyethylene, propyleneoxypropylene, butyleneoxybutylene, 1,2-propyleneoxy-1,2-propylene, 2,3-butylene-oxy-2,3-butylene, hexyleneoxyhexylene, 2-ethyl-hexyleneoxy-2-ethyl-hexylene, ethyleneoxypropylene and ethyleneoxybutylene.

The R—[—CH$_2$—O—]$_n$ group is derived from a dihydric, trihydric, tetrahydric, pentahydric or hexahydric alcohol or oxy alkylene ether, wherein R is hydrogen, alkyl having from one to about eight carbon atoms, or alkyleneoxyalkylene, each alkylene having from two to about eight carbon atoms.

Exemplary are glycerol, trimethylolethane, trimethylolpropane, pentaerythritol, ditrimethylolethane, ditrimethylolpropane, dipentaerythritol, diglycerol, sorbitol and mannitol. The preferred polyhydric alcohols have the neopentyl structure, such as the trimethylolalkanes, the ditrimethylolalkanes, pentaerythritol, and dipentaerythritol.

Exemplary compounds within the invention include:

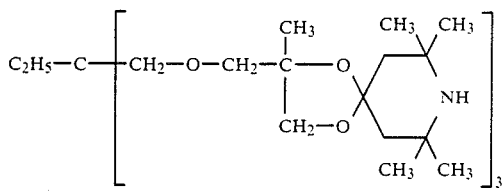

| | Derived from Polyhydric Alcohol |
|---|---|
| 10. 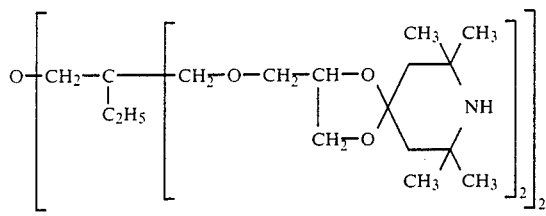 | Di(trimethylol propane) |
| 11. 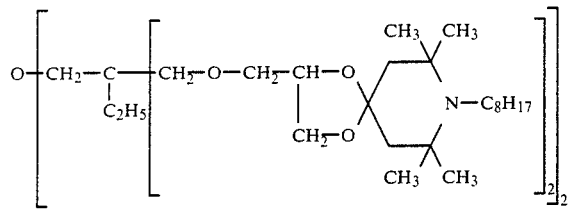 | Dipentaerythritol |
| 12. 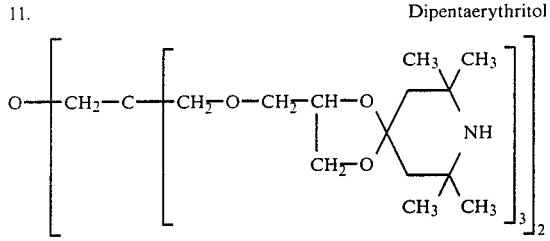 | Dipentaerythritol |
| 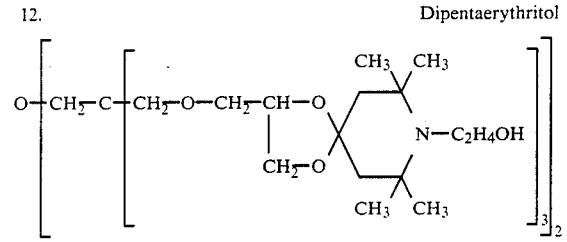 | |

These compounds can be easily prepared by the reaction of corresponding 2,3-dihydroxypropyl derivatives obtained by hydrolysis of the (methyl)glycidyl ether of the corresponding polyhydric alcohol with 2,2,6,6-tetramethylpiperidine in the presence of an acid catalyst. The following Example is illustrative:

EXAMPLE I

Preparation of

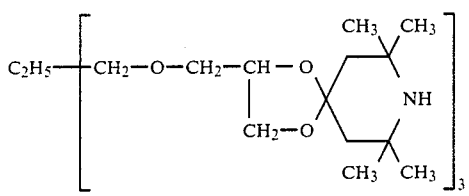

Tris(2,3-dihydroxypropoxymethyl)propane was prepared as a pale yellow liquid by hydrolyzing trimethylol propane triglycidyl ether in the presence of sulfuric acid. Tris(2,3-dihydroxypropoxymethyl)propane 3.0 g, 2,2,6,6-tetramethyl-4-piperidone hydrochloride 5.8 g, p-toluene sulfonic acid 0.3 g and 2-butanol 60 ml were heated and stirred at 90° C. for 10 hours while the water produced was removed by azeotropic distillation employing n-hexane as a carrier.

Then 10% aq. NaOH solution 30 ml was added and the mixture stirred. The organic layer was decanted, and the solvent distilled off. Toluene was added, and the solution was filtered through a layer of Kyowaad 700 (Kyowa Chemical Co., synthetic absorbent). The solvent was distilled, and 2.7 g of light brown viscous liquid was obtained. I.R. analysis of the product showed absorption at 1100 cm$^1$ corresponding to the ketal bond and at 3200–3300 cm$^1$ corresponding to the NH bond, confirming the structure to be as set out above.

| | Elemental analysis | | |
|---|---|---|---|
| | C % | H % | N % |
| Found | 65.56 | 10.10 | 5.42 |
| Calcd. (as $C_{42}H_{77}N_3O_9$) | 65.71 | 10.04 | 5.48 |

Small amounts of the polyhydric alcohol ethers of this invention when combined with synthetic resin improve the light stability of the resin. The amount of the polyhydric alcohol ethers is generally within the range from about 0.001 to about 5 parts by weight, preferably from about 0.01 to about 3 parts by weight, per 100 parts by weight of resin.

Synthetic resins that can have their resistance to deterioration enhanced with the polyhydric alcohol ethers according to this invention include α-olefin polymers such as polyethylene, polypropylene, polybutene, poly-3-methylbutene, or mixtures thereof, and copolymers with other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The polyhydric alcohol ethers of the invention can be combined with conventional heat stabilizers such as phenolic antioxidants, polyvalent metal salts of organic acids, organic phosphites, thioethers, and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

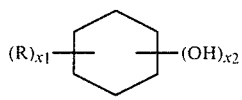

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

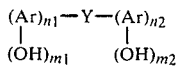

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

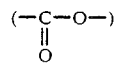

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

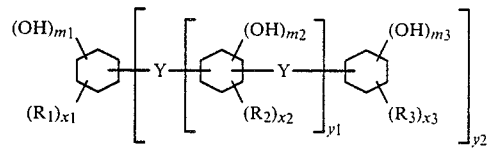

wherein $R_1$, $R_2$ and $R_3$ are inert substituent groups as described in the previous paragraph;

$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

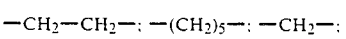

-continued

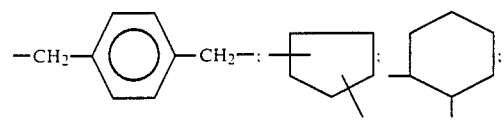
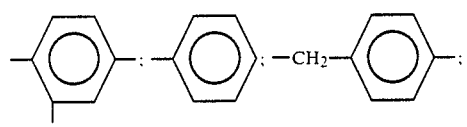
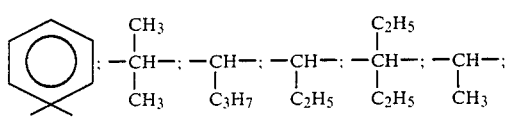
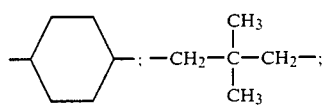
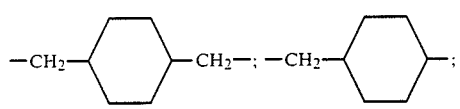
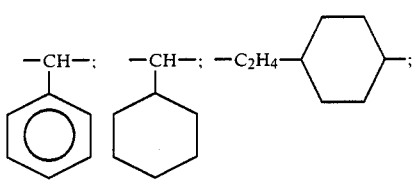
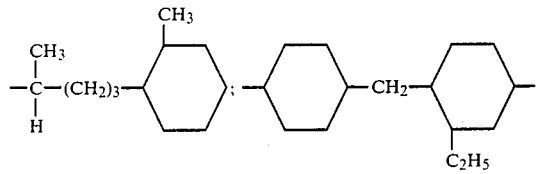
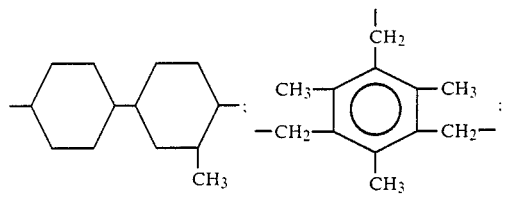
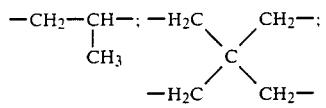
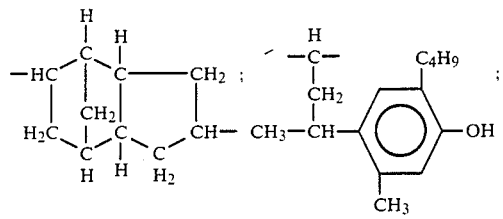

(2) Y groups where only atoms other than carbon link the aromatic rings, such as —O—, —S—,
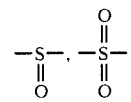

and —(S)$_x$— where x is a number from one to ten;

(3) Y groups made up of more than a single atom including both carbon and other atoms linking the aromatic nuclei, such as:

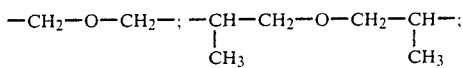
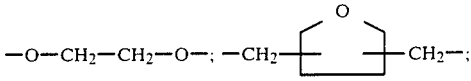
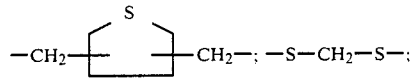
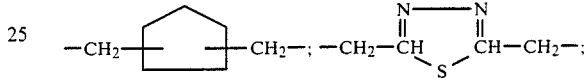
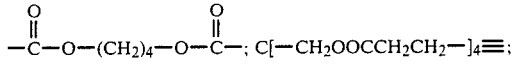
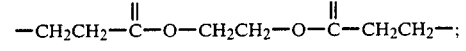
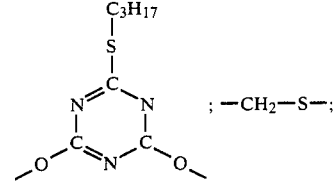
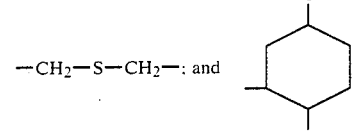

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenyl, tetrahydro-α-naphthol, o-, m- and p-cresol, o-, m- and p-phenylphenol, o-, m- and p-xylenols, the carvenols, symmetrical xylenol, thymol, o-, m- and p-nonylphenol, o-, m- and p-dodecyl-pheno, and o-, m- and p-octyl-phenol, o-, and m-tert-butyl-p-hydroxy-anisole, p-n-decyloxy-phenol, p-n-decyloxy-cresol, nonyl-n-decyloxycresol, eugenol, isoeugenol, glyceryl monosalicylate, methyl-p-hydroxy-cinnamate, 4-benzyloxy-phenol, p- acetylaminophenol, p-stearyl-aminophenol, methyl-p-hydroxybenzoate, p-di-chlorobenzoyl-aminophenol, p-hydroxysalicyl anilide, -stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl(4-hydroxy-3-methyl-5-t-butyl)benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexylcatechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis(2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol, 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methylphenol), 2,2'-methylene-bis-(4-methyl-6-(1'-methyl-cyclohexyl)phenol), 4,4'-cyclohexylene bis-(2-tertiary-butyl-phenol), 2,6-bis-(2'-hydroxy-3'-t-butyl-5'-methyl-benzyl)-4-methyl-phenol, cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl)sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methyl-benzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid]glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis[methylene-3-(3,5-di-t-butyl-4-hydroxyphenyl)propionate]methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

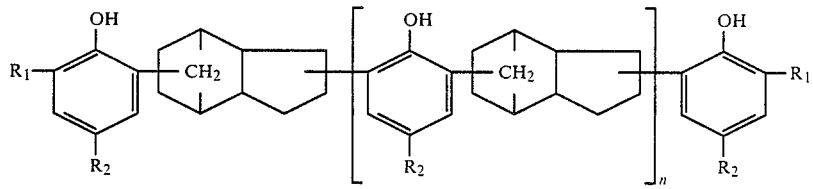

4,4'-oxobis(naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl) propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxy-phenyl)(3',5'-di-tert-butyl-4',4-hydroxyphenyl)ethane, 2,2'-methylene-bis-(4-octylphenol), 4,4'-propylene-bis-(2-tert-butyl-phenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole. 4,4'-bis-(4-hydroxyphenyl)pentanoic acid octadecyl ester, cyclopentylene-4,4'-bis-phenol, 2-ethylbutylene-4,4'-bisphenol, 4,4'- in which

R₁ and R₂ are lower alkyl, and can be the same or different, and n is the number of the groups enclosed by the brackets, and is usually from 1 to about 5.

These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

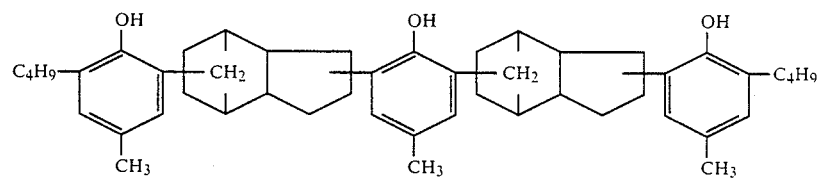

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

When the polyhydric alcohol ether is used with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocylic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is 15 is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophosphites.

The organic triphosphites in which the radicals are monovalent radicals can be defined by the formula:

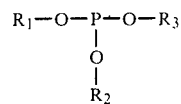

in which
$R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

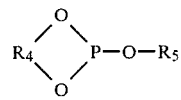

in which
$R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$;
$R_5$ is hydrogen or a cation, in the case of the acid phosphites.

Also useful organic triphosphites are mixed heterocyclic-open chain phosphites of the type:

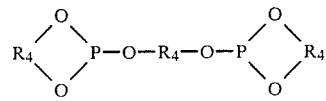

More complex triphosphites are formed from trivalent organic radicals, of the type:

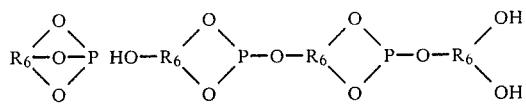

in which
$R_6$ is a trivalent organic radical of any of the types of $R_1$ to $R_5$, inclusive, as defined above.

A particularly useful class of complex triphosphites are the tetraoxadiphosphaspiro undecanes of the formula:

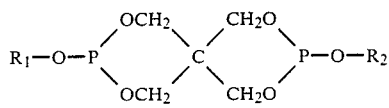

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

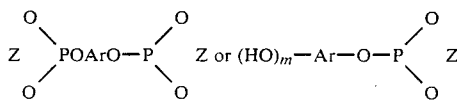

in which

Ar is a mono or bicyclic aromatic nucleus and m is an integer of from 0 to about 5.

Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, pheny dicyclohexyl phosphite, phenyl diethyl phosphite, triphenyl phosphite, tricresyl phosphite, tri(dimethylphenyl)phoshite, trioctadecyl phosphite, triisooctyl phosphite, tridodecyl phosphite, isooctyl diphenyl phosphite, diisooctyl phenyl phosphite, tri(t-octylphenyl)phosphite, tri-(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-cyclohexylphenyl)phosphite), tri-α-naphthyl phosphite, tri(phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane(diphenyl-pentaerythritol diphosphite), 3,9-di(decyloxy)-2,4,8,10-tetraoxa-3,9-diphosphaspiro(5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di-(butoxyethoxyethyloxy)-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy)ethyloxy group has an average molecular weight of 350), 3,9-di(methoxy(polyethoxy)ethyloxy)-2,4,8,10-tetraoxa-3,9-diphosphaspiro-(5,5)-undecane (where the (polyethoxy)ethyloxy group has an average molecular weight of 550).

Exemplary of the bis aryl triphosphites are: bis(4,4'-thio-bis(2-tertiary-butyl-5-methyl-phenol))isooctyl phosphite, mono(4,4'-thio-bis(2-tertiary-butyl-5-methyl-phenol))di-phenyl phosphite, tri-(4,4'-n-butylidene-bis(2-tertiary-butyl-5-methyl-phenol))phosphite, (4,4'-benzylidene-bis(2-tertiary-butyl-5-methyl-phenol))diphenyl phosphite, isooctyl 2,2'-bis(-parahydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl-(2,6-bis(2'-hydroxy-3,5-dinonylbenzyl)-4-nonyl phenyl))phosphite, tetra-tridecyl-4,4'-n-butylidene-bis(2-tertiary-butyl-5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bisphenyl polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiarybutyl-5-methylphenyl)diphosphite, tetra-tridecyl-4,4'-isopropylidene bisphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, dicresyl phosphite, di-(o-isooctylphenyl)phosphite, di(p-ethylhexylphenyl)phosphite, di(p-t-octylphenyl)phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol))- phosphite, (4,4'-thio-bis(2-tertiary-butyl-5-methylphenol))phenyl phosphite, bis(4,4'-n-butylidene-bis(2-tertiary-butyl-5-methylphenol))phosphite, mono(4,4'-benzylidene-bis(2-tertiary-butyl-5-methylphenol))-phosphite, mono(2,2'-bis-(parahydroxyphenyl)-propane)phosphite, mono(4,4'-butylidene-bis(2-tertiary-butyl-5-methylphenol)phosphite, bis(4,4'-thio-bis(2-tertiary-butyl-5-methylphenol))phosphite, mono-2-ethylhexyl-mono-2,2'-methylene-bis(4-methyl-6,1'-methyl-cyclohexyl)phenol phosphite, bis(2,2'-bis(para-hydroxyphenyl)propane)phosphite, monoisooctyl-mono(4,4'-thio-bis(2-tertiary-butyl-5-methylphenol))phosphite, isooctyl-(2,6-bis(2'-hydroxy-3,5-dinonylbenzyl)-4-nonylphenyl))phosphite, tri-tridecyl-4,4'-n-butylidene-bis(2-tertiary-butyl-5-methylphenyl)diphosphite, triisooctyl-4,4'-thio-bis(2-tertiary-butyl-5-methylphenyl)-diphosphite, bis(2,2'-methylene-bis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene-bis(2-tertiary-butyl-5-methylphenyl)diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

$$R_1OOCCH_2CH_2-S-CH_2CH_2COOY$$

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

$$-XO[OCCH_2CH_2SCH_2CH_2COOXO]_nOCCH_2CH_2-S-CH_2CH_2COOZ$$

where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylene-arylene and mixed alkylene-cycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:
(a) $R_1OOCCH_2CH_2SCH_2CH_2COOH$
(b) $R_1OOCCH_2CH_2SCH_2CH_2COOR_2$
(c) $R_1O[OCCH_2CH_2SCH_2CH_2COOX-O]_nOCCH_2CH_2SCH_2CH_2COOZ$
(d) $R_1OOCCH_2CH_2SCH_2CH_2COOM$ In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

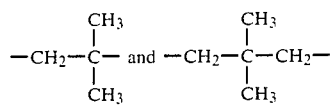

arylene radicals such as phenylene

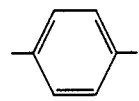

methylenephenylene

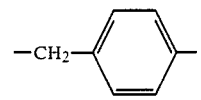

dimethylene phenylene

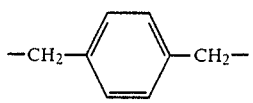

and alicyclylene such as cyclohexylene

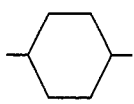

and cyclopentylene

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

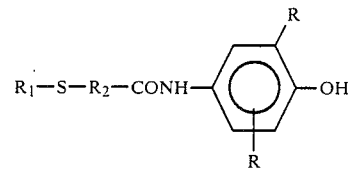

R is alkyl of one to eight carbon atoms,
$R_1$ is alkyl of six to twenty-four carbon atoms, and $R_2$ is alkylene of one to six carbon atoms.

(2) Thioalkanoic acid amides of 1,3,5-triazines of Ozeki et al Japanese Pat. No. 20,366/68 having the formula:

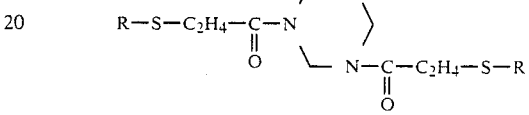

R is alkyl of eight to eighteen carbon atoms.

(3) Bis-thioalkanoic acid amides of Yamamoto et al Japanese Pat. No. 23,765/68 having the formula:

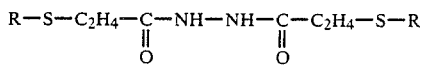

R is alkyl of more than six carbon atoms, aryl or aralkyl.

(4) Bis-thioalkylanoic acid amides of Ozeki et al Japanese Pat. No. 26,184/69 having the formula:

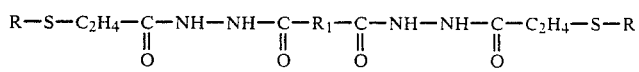

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese Pat. No. 31,464/69 having the formula:

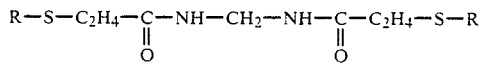

R is alkyl or more than six carbon atoms, aryl, or aralkyl.

(6) Thioalkanoic acid amide derivatives of Minagawa et al, published Japanese application No. 106,484/74 having the formula:

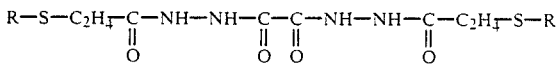

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

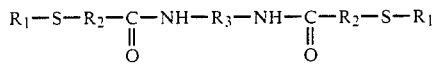

wherein:
R₁ is alkyl having from one to about fifty carbon atoms;
R₂ is alkylene having from one to about three carbon atoms; and
R₃ is alkylene having from about two to about twelve carbon atoms.

β-Alkylthiopropionic acid esters having the general formula:

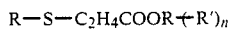

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxy benzophenone, 2,4-dihydroxybenzophenone, benzotriazoles, such as 2(2-hydroxy-5-methylphenyl)benzotriazoles, 2(2-hydroxy-3-t-butyl-5-methylphenyl)-5-chlorobenzotriazole, 2(2-hydroxy-3-5-di-t-butylphenyl)5-chlorobenzotriazole, 2(2-hydroxy-3,5-di-t-amylphenyl)benzotriazole, benzoates such as phenylsalicylate, 2,4-di-t-butylphenyl-3,5-di-t-butyl-4-hydroxy phenylbenzoate, nickel compounds such as nickel-2,2'-thiobis(4-t-octylphenolate), nickel-monoethyl(3,5-di-t-butyl-4-hydroxybenzyl)phosphonate, substituted acrylonitriles such as methyl-α-cyano-β-methyl-β-(p-methoxy phenyl)acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 10% total stabilizers including the polyhydric alcohol ether by weight of the polymer are satisfactory. Preferably, from 0.01 to 5% is employed for optimum stabilization.

The stabilizer systems of the invention are readily rendered in solid particulate form, comprising a blend of:
(a) polyhydric alcohol ether light stabilizer in an amount of from about 10 to about 35 parts by weight; and optionally:
(b) a phenolic antioxidant in an amount from about 10 to about 35 parts by weight; and/or
(c) other heat or light stabilizers in an amount of from about 10 to about 35 parts by weight.

The polyhydric alcohol ethers of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement or ageing and heating.

The following Examples in the opinion of the inventors represent preferred embodiments of synthetic resin compositions containing the polyhydric alcohol ether stabilizers of the invention.

EXAMPLES 1 TO 5

Polypropylene compositions were prepared using stabilizers of the invention and two of the prior art, and having the following formulation:

| Ingredient | Parts by Weight |
|---|---|
| Polypropylene | 100 |
| Stearyl β-3,5-di-tert-butyl-4-hydroxyphenyl propionate | 0.2 |
| Stabilizer as shown in Table I | 0.3 |

The compositions were thoroughly blended in a Brabender Plastograph, and then compression-molded to form sheets 0.3 mm thick. Pieces 2.5 cm² were cut off from the sheets, and exposed to a high voltage mercury lamp.

Additional 2.5 cm² pieces from the same sheets were exposed to a high voltage mercury lamp for 100 hours; immersed in hot water at 80° C. for 15 hours; and then exposed again to a high voltage mercury lamp until failure. The hours to failure were noted, and are shown in Table I.

TABLE I

| Example No. | Stabilizer | Hours to Failure Without Immersion | Hours to Failure After Immersion for 15 hours |
|---|---|---|---|
| Control 1 | 1,2-Bis(8-aza-7,7,8,9,9-pentamethyl-1,4-dioxaspiro[4,5]-2-decylmethoxy)ethane | 370 | 260 |
| Control 2 | Tris(8-aza-7,7,8,9,9-pentamethyl-1,4-dioxaspiro[4,5]-2-decylmethyl)trimesate | 430 | 290 |
| Example 1 | $C_2H_5-C+CH_2-O-CH_2-CH(CH_2-O-)-O-C(CH_3)_2-CH_2-NH-CH_2-C(CH_3)_2$ (spiro structure) — trimer | 670 | 590 |
| Example 2 | $CH_3-C+CH_2-O-CH_2-CH(CH_2-O-)-O-C(CH_3)_2-CH_2-NH-CH_2-C(CH_3)_2$ — trimer | 660 | 580 |
| Example 3 | $C+CH_2-O-CH_2-CH(CH_2-O-)-O-C(CH_3)_2-CH_2-N(CH_3)-CH_2-C(CH_3)_2$ — tetramer | 710 | 640 |
| Example 4 | $O+CH_2-C(C_2H_5)+CH_2-O-CH_2-CH(CH_2-O-)-O-C(CH_3)_2-CH_2-NH-CH_2-C(CH_3)_2$ (×2)$_2$ | 700 | 610 |
| Example 5 | $O+CH_2-C+CH_2-O-CH_2-CH(CH_2-O-)-O-C(CH_3)_2-CH_2-NH-CH_2-C(CH_3)_2$ (×3)$_2$ | 690 | 600 |

The compounds of the invention are far superior to the prior art compounds.

EXAMPLES 6 TO 10

Conventional stabilizers for polymeric materials may lose their effectiveness because of volatilization or decomposition at high polymer processing temperatures. This is not true of the stabilizers of the invention, as shown by observing the effect of heat in repeated extrusions of ethylenepropylene copolymer compositions. These compositions were prepared using stabilizers of the invention and of the prior art, and having the following formulation:

| Ingredient | Parts by Weight |
|---|---|
| Ethylene-propylene copolymer | 100 |
| Ca stearate | 0.2 |
| Stearyl-(3,5-di-t-butyl-4-hydroxyphenyl) propionate | 0.1 |
| Dilauryl thiodipropionate | 0.2 |
| Stabilizer as shown in Table II | 0.2 |

The ingredients were mixed and the compositions then extruded (cylinder temperature 230° C. and 240° C., head die temperature 250° C., velocity 20 rpm) five times. Test pieces were then molded by injection molding at 250° C. The test pieces were exposed to a high voltage mercury lamp, and the hours to failure were noted, and are shown in Table II.

TABLE II

| Example No. | Stabilizer | Hours to Failure Extruded 1 time | Hours to Failure Extruded 5 times |
|---|---|---|---|
| Control 1 | 1,2-Bis(8-aza-7,7,8,9,9-pentamethyl-1,4-dioxaspiro[4.5]-2-decylmethoxy)ethane | 280 | 160 |
| Control 2 | Tris(8-aza-7,7,8,9,9-pentamethyl-1,4-dioxaspiro[4.5]-2-decylmethyl)trimesate | 310 | 170 |
| Example 6 | [structure] | 520 | 450 |
| Example 7 | [structure] | 550 | 490 |
| Example 8 | [structure] | 540 | 490 |
| Example 9 | [structure] | 510 | 450 |
| Example 10 | [structure] | 520 | 470 |

The compounds of the invention are far superior to the prior art compunds.

EXAMPLES 11 TO 16

High density polyethylene compositions were prepared using the stabilizers of the invention and two of the prior art, and having the following formulation.

| Ingredient | Parts by Weight |
|---|---|
| High-density polyethylene | 100 |
| Ca stearate | 1.0 |
| Tetrakis(methylene-3-(3,5-di-t-butyl-4-hydroxyphenyl) propionate) methane | 0.1 |
| Distearylthiodipropionate | 0.3 |
| Stabilizer as shown in Table III | 0.2 |

The stabilizer was blended with the polymer on a two-roll mill and sheets 0.5 mm thick were prepared by compression molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table III.

TABLE III

| Example No. | Stabilizer | Hours to Failure |
|---|---|---|
| Control 1 | 1,2-Bis(8-aza-7,7,8,9,9-pentamethyl-1,4-dioxaspiro[4,5]-2-decylmethoxy)ethane | 610 |
| Control 2 | Tris(8-aza-7,7,8,9,9-pentamethyl-1,4-dioxaspiro[4,5]-2-decylmethyl)trimesate | 680 |
| Example 11 | $C_2H_5-C+CH_2-O-CH_2-CH-O-\text{(2,2,6,6-tetramethylpiperidin-4-yl, NH, spiro with }CH_2-O\text{)}]_3$ | 1,060 |
| Example 12 | $C_2H_5-C+CH_2-O-CH_2-C(CH_3)-O-\text{(2,2,6,6-tetramethylpiperidin-4-yl, NH, spiro with }CH_2-O\text{)}]_3$ | 1,020 |
| Example 13 | $CH_3-C+CH_2-O-CH_2-CH-O-\text{(2,2,6,6-tetramethylpiperidin-4-yl, NO·, spiro with }CH_2-O\text{)}]_3$ | 1,050 |
| Example 14 | $C+CH_2-O-CH_2-CH-O-\text{(2,2,6,6-tetramethylpiperidin-4-yl, N-}CH_3\text{, spiro with }CH_2-O\text{)}]_4$ | 1,140 |
| Example 15 | $O+CH_2-C(C_2H_5)+CH_2-O-CH_2-CH-O-\text{(2,2,6,6-tetramethylpiperidin-4-yl, NH, spiro with }CH_2-O\text{)}]_2]_2$ | 1,100 |
| Example 16 | $O+CH_2-C+CH_2-O-CH_2-CH-O-\text{(2,2,6,6-tetramethylpiperidin-4-yl, N-}C_2H_4OH\text{, spiro with }CH_2-O\text{)}]_3]_2$ | 1,090 |

The compounds of the invention are far superior to the prior art compounds.

EXAMPLES 17 TO 21

Ethylene-vinyl acetate copolymer compositions were prepared using stabilizers of the invention and two of the prior art, and having the following formulation.

| Ingredient | Parts by Weight |
|---|---|
| Ethylene-vinyl acetate copolymer | 100 |
| 2,6-Di-t-butyl-p-cresol | 0.1 |
| Ca stearate | 0.1 |
| Zn stearate | 0.1 |
| Diisodecylphenylphosphite | 0.2 |
| Stabilizer as shown in Table IV | 0.2 |

The stabilizer was blended with the polymer on a two-roll mill at 130° C., and sheets 0.4 mm thick were then compression molded at 140° C. from the resulting blend.

Pieces 2.5 cm square were cut off from the sheets, and exposed to ultraviolet light in a Weather-O-Meter for 500 hours. At the start and at the conclusion of the test, tensile strength of the sheet samples was determined. The results are shown in Table IV as % retention of the initially determined tensile strength.

| Ingredient | Parts by Weight |
|---|---|
| Polyvinyl chloride | 100 |
| Dioctylphthalate | 48 |
| Epoxidized soybean oil | 2 |
| Tris nonylphenyl phosphite | 0.2 |
| Ca stearate | 1.0 |
| Zn stearate | 0.1 |
| Stabilizer as shown in Table V | 0.3 |

TABLE IV

| Example No. | Stabilizer | % Retention of Tensile Strength After 500 Hours |
|---|---|---|
| Control 1 | 1,2-Bis(8-aza-7,7,8,9,9-pentamethyl-1,4-dioxaspiro[4,5]-2-decylmethoxy)ethane | 60 |
| Control 2 | Tris(8-aza-7,7,8,9,9-pentamethyl-1,4-dioxaspiro[4,5]-2-decylmethyl)trimesate | 63 |
| Example 17 | $C_2H_5-C{+\!\!\!\!+} CH_2-O-CH_2-CH-O-[8\text{-aza-}7,7,8,9,9\text{-pentamethyl-1,4-dioxaspiro}[4,5]\text{-2-decyl, N-CH}_3]\}_3$ | 78 |
| Example 18 | $CH_3-C{+\!\!\!\!+} CH_2-O-CH_2-CH-O-[8\text{-aza-}7,7,8,9,9\text{-pentamethyl-1,4-dioxaspiro}[4,5]\text{-2-decyl, NH}]\}_3$ | 76 |
| Example 19 | $C{+\!\!\!\!+} CH_2-O-CH_2-CH-O-[8\text{-aza-}7,7,8,9,9\text{-pentamethyl-1,4-dioxaspiro}[4,5]\text{-2-decyl, NH}]\}_4$ | 81 |
| Example 20 | $O{+\!\!\!\!+} CH_2-C(C_2H_5){+\!\!\!\!+} CH_2-O-CH_2-CH-O-[8\text{-aza-}7,7,8,9,9\text{-pentamethyl-1,4-dioxaspiro}[4,5]\text{-2-decyl, N-C}_8H_{17}]_2\}_2$ | 75 |
| Example 21 | $O{+\!\!\!\!+} CH_2-C{+\!\!\!\!+} CH_2-O-CH_2-CH-O-[8\text{-aza-}7,7,8,9,9\text{-pentamethyl-1,4-dioxaspiro}[4,5]\text{-2-decyl, N-C}_2H_4OH]_3\}_2$ | 76 |

The compounds of the invention are far superior to the prior art compounds.

EXAMPLES 22 TO 26

A group of polyvinyl chloride resin compositions was prepared having the following formulation:

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light. The results obtained are shown in Table V.

TABLE V

| Example No. | Stabilizer | Hours to Failure |
|---|---|---|
| Control 1 | None | 200 |
| Control 2 | 1,2-Bis(8-aza-7,7,8,9,9-pentamethyl-1,4-dioxaspiro[4,5]-2-decylmethoxy)ethane | 290 |
| Control 3 | Tris(8-aza-7,7,8,9,9-pentamethyl-1,4-dioxaspiro[4,5]-2-decylmethyl)trimesate | 350 |
| Example 22 | $\left[C_2H_5-C-\left(CH_2-O-CH_2-CH-O-\underset{CH_2-O}{\underset{|}{\phantom{X}}}\text{(piperidinyl, N--CH}_3\text{)}\right)\right]_3$ | 680 |
| Example 23 | $\left[CH_3-C-\left(CH_2-O-CH_2-CH-O-\text{(piperidinyl, NO·)}\right)\right]_3$ | 700 |
| Example 24 | $\left[C-\left(CH_2-O-CH_2-CH-O-\text{(piperidinyl, N--C(=O)CH}_3\text{)}\right)\right]_4$ | 710 |
| Example 25 | $\left[O-\left(CH_2-\underset{C_2H_5}{\underset{|}{C}}-\left(CH_2-O-CH_2-CH-O-\text{(piperidinyl, N--C}_8H_{17}\text{)}\right)_2\right)\right]_2$ | 660 |
| Example 26 | $\left[O-\left(CH_2-C-\left(CH_2-O-CH_2-CH-O-\text{(piperidinyl, N--C}_2H_4OH\text{)}\right)_3\right)\right]_2$ | 690 |

The compounds of the invention are far superior to the prior art compounds.

EXAMPLES 27 TO 31

Acrylonitrile-butadiene-styrene terpolymer resin compositions were prepared using stabilizers of the invention and two of the prior art, and having the following formulation:

| Ingredient | Parts by Weight |
|---|---|
| Acrylonitrile-butadiene-styrene terpolymer | 100 |
| 4,4'-butylidenebis(2-t-butyl-m-cresol) | 0.1 |
| Stabilizer as shown in Table VI | 0.3 |

The stabilizer was blended with the resin on a two-roll mill, and sheets 3 mm thick were prepared by compression molding of the resulting blend. Pieces 2.5 cm square were cut off from the sheets, and subjected to ulraviolet light in a Weather-O-Meter for 800 hours.

Tensile strength before and after the test exposure was determined, and the results are reported as the % of tensile strength retained in Table VI.

TABLE VI

| Example No. | Stabilizer | % Tensile Strength Retained |
|---|---|---|
| Control 1 | 1,2-Bis(8-aza-7,7,8,9,9-pentamethyl-1,4-dioxaspiro[4.5]-2-decylmethoxy)ethane | 51 |
| Control 2 | Tris(8-aza-7,7,8,9,9-pentamethyl-1,4-dioxaspiro[4.5]-2-decylmethyl)trimesate | 55 |
| Example 27 | $C_2H_5-C{\left[-CH_2-O-CH_2-CH(-CH_2-O-)-O-\text{(2,2,6,6-tetramethylpiperidin-4-yl)}\right]}_3$ | 77 |
| Example 28 | $C_2H_5-C{\left[-CH_2-O-CH_2-C(CH_3)(-CH_2-O-)-O-\text{(2,2,6,6-tetramethylpiperidin-4-yl)}\right]}_3$ | 72 |
| Example 29 | $CH_3-C{\left[-CH_2-O-CH_2-CH(-CH_2-O-)-O-\text{(2,2,6,6-tetramethylpiperidin-4-yl)}\right]}_3$ | 76 |
| Example 30 | $C{\left[-CH_2-O-CH_2-CH(-CH_2-O-)-O-\text{(2,2,6,6-tetramethylpiperidin-4-yl)}\right]}_4$ | 77 |
| Example 31 | $O{\left[-CH_2-C{\left[-CH_2-O-CH_2-CH(-CH_2-O-)-O-\text{(2,2,6,6-tetramethylpiperidin-4-yl)}\right]}_3\right]}_2$ | 75 |

The compounds of the invention are far superior to the prior art compounds.

EXAMPLES 32 TO 36

Polyurethane resin compositions were prepared using stabilizers of the invention and of the prior arts and having the following formulation:

| Ingredient | Parts by Weight |
|---|---|
| Polyurethane resin(Asahi Denka[1]; U-100) | 100 |
| Ba stearate | 0.7 |
| Zn stearate | 0.3 |
| 2,6-di-t-butyl-p-cresol | 0.1 |
| Stabilizer as shown in Table VII | 0.3 |

[1] A polyurethane resin made from toluenediisocyanate and alkylene polyol

The stabilizers were blended with the finely powdered polyurethane resin on a two-roll mill for five minutes at 70° C., and the sheets were then compression-molded at 120° C. for five minutes, to form sheets 0.5 mm thick.

Pieces 2.5 cm square were cut off from the sheets, and exposed to ultraviolet light in a Weather-O-Meter for 30 hours. Elongation before and after the exposure was determined, and the % elongation retained after the exposure is given in Table VII.

TABLE VII

| Example No. | Stabilizer | % Elongation Retained |
|---|---|---|
| Control 1 | 1,2-Bis(8-aza-7,7,8,9,9-pentamethyl-1,4-dioxaspiro[4,5]-2-decylmethoxy)ethane | 49 |
| Control 2 | Tris(8-aza-7,7,8,9,9-pentamethyl-1,4-dioxaspiro[4,5]-2-decylmethyl)trimesate | 53 |
| Example 32 | $C_2H_5-C\left[CH_2-O-CH_2-CH(CH_2\!-\!O)-O-\text{(2,2,6,6-tetramethylpiperidin-4-yl ketal)}\,NH\right]_3$ | 74 |
| Example 33 | $C_2H_5-C\left[CH_2-O-CH_2-CH(CH_2\!-\!O)-O-\text{(2,2,6,6-tetramethylpiperidin-4-yl ketal)}\,N\!-\!CH_3\right]_3$ | 75 |
| Example 34 | $C\left[CH_2-O-CH_2-CH(CH_2\!-\!O)-O-\text{(2,2,6,6-tetramethylpiperidin-4-yl ketal)}\,NH\right]_4$ | 77 |
| Example 35 | $C\left[CH_2-O-CH_2-CH(CH_2\!-\!O)-O-\text{(2,2,6,6-tetramethylpiperidin-4-yl ketal)}\,N\!-\!C(=\!O)CH_3\right]_4$ | 71 |
| Example 36 | $O\left[CH_2-C(C_2H_5)\left[CH_2-O-CH_2-CH(CH_2\!-\!O)-O-\text{(2,2,6,6-tetramethylpiperidin-4-yl ketal)}\,N\!-\!C_8H_{17}\right]_2\right]_2$ | 71 |

The compounds of the invention are far superior to the prior art compounds.

Having regard to the foregoing disclosure, the following is claimed as the inventive and patentable embodiments thereof:

1. Polyhydric alcohol ethers of 2,2,6,6-tetramethyl-4-piperidone ketals having the formula:

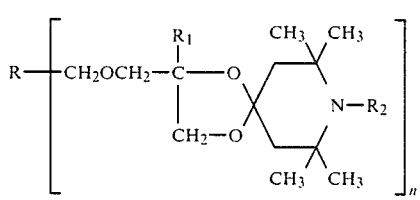

wherein:

R is selected from the group consisting of alkylene having from one to about eight carbon atoms and alkyleneoxyalkylene in which each alkylene has from two to about eight carbon atoms;

$R_1$ is selected from the group consisting of hydrogen and alkyl having from one to about four carbon atoms;

$R_2$ is selected from the group consisting of hydrogen; oxyl O; alkyl, hydroxy alkyl and epoxyalkyl having from one to about eighteen carbon atoms; acyl having from one to about eighteen carbon atoms; cycloalkyl having from three to about eighteen carbon atoms; phenyl; phenalkyl and alkylphenyl having from seven to about twenty-four carbon atoms; and n is a number from 3 to 6.

2. Polyhydric alcohol ethers according to claim 1 in which R is alkylene and $R_1$ and $R_2$ are each hydrogen.

3. Polyhydric alcohol ethers according to claim 1 in which R is alkyleneoxyalkylene and $R_1$ and $R_2$ are each hydrogen.

4. Polyhydric alcohol ethers according to claim 1 in which $R_2$ is hydrogen.

5. Polyhydric alcohol ethers according to claim 1 in which $R_2$ is O.

6. Polyhydric alcohol ethers according to claim 1 in which $R_2$ is alkyl.

7. Polyhydric alcohol ethers according to claim 1 wherein $R_2$ is hydroxyalkyl.

8. Polyhydric alcohol ethers according to claim 1 wherein $R_2$ is epoxyalkyl.

9. Polyhydric alcohol ethers according to claim 1 wherein $R_2$ is acyl.

10. Polyhydric alcohol ethers according to claim 1 wherein n is 3.

11. Polyhydric alcohol ethers according to claim 1 wherein n is 4.

12. Polyhydric alcohol ethers according to claim 1 having the formula:

$$C_2H_5-C\left[\!-CH_2-O-CH_2-\underset{\underset{CH_2-O}{|}}{CH}-O\!-\!\!\!\left\langle\!\!\begin{array}{c}CH_3\quad CH_3\\ \\ CH_3\quad CH_3\end{array}\!\!\right\rangle\!NH\right]_3$$

13. Polyhydric alcohol ethers according to claim 1 having the formula:

$$C_2H_5-C\left[\!-CH_2-O-CH_2-\underset{\underset{CH_2-O}{|}}{CH}-O\!-\!\!\!\left\langle\!\!\begin{array}{c}CH_3\quad CH_3\\ \\ CH_3\quad CH_3\end{array}\!\!\right\rangle\!N-CH_3\right]_3$$

14. Polyhydric alcohol ethers according to claim 1 having the formula:

$$C\left[\!-CH_2-O-CH_2-\underset{\underset{CH_2-O}{|}}{CH}-O\!-\!\!\!\left\langle\!\!\begin{array}{c}CH_3\quad CH_3\\ \\ CH_3\quad CH_3\end{array}\!\!\right\rangle\!NH\right]_4$$

15. Polyhydric alcohol ethers according to claim 1 having the formula:

$$C\left[\!-CH_2-O-CH_2-\underset{\underset{CH_2-O}{|}}{CH}-O\!-\!\!\!\left\langle\!\!\begin{array}{c}CH_3\quad CH_3\\ \\ CH_3\quad CH_3\end{array}\!\!\right\rangle\!N-CH_3\right]_4$$

16. Polyhydric alcohol ethers according to claim 1 having the formula:

$$O\!\!-\!\!\left[\!-CH_2-\underset{\underset{C_2H_5}{|}}{C}\!-\!\!\left[\!-CH_2-O-CH_2-\underset{\underset{CH_2-O}{|}}{CH}-O\!-\!\!\!\left\langle\!\!\begin{array}{c}CH_3\quad CH_3\\ \\ CH_3\quad CH_3\end{array}\!\!\right\rangle\!NH\right]_2\right]_2$$

17. A polyvinyl chloride resin composition having improved resistance to deterioration upon exposure to light comprising a polyvinyl chloride resin formed at least in part of the recurring group:

$$-\underset{\underset{Cl}{|}}{CH}-\underset{\underset{X}{|}}{\overset{\overset{X}{|}}{C}}-$$

and having a chlorine content in excess of 40%, where X is either hydrogen or chlorine; and a compound in accordance with claim 1.

18. A polyvinyl chloride resin composition in accordance with claim 17 in which the polyvinyl chloride resin is polyvinyl chloride homopolymer.

19. A polyvinyl chloride resin composition in accordance with claim 17 in which the polyvinyl chloride resin is a copolymer of vinyl chloride and vinyl acetate.

20. An olefin polymer composition having improved resistance to deterioration upon exposure to light comprising an olefin polymer selected from the group consisting of polymers of alpha-olefins having from two to six carbon atoms and polystyrene, and a compound in accordance with claim 1.

21. An olefin polymer composition in accordance with claim 20 wherein the polyolefin is polypropylene.

22. An olefin polymer composition in accordance with claim 20 wherein the polyolefin is polyethylene.

23. An olefin polymer composition in accordance with claim 20 wherein the polyolefin is ethylene-propylene copolymer.

24. A polyurethane resin composition having improved resistance to deterioration upon exposure to light comprising a polyurethane resin and a compound in accordance with claim 1.

25. An ethylene-vinyl acetate copolymer composition having improved resistance to deterioration upon exposure to light comprising an ethylene-vinyl acetate copolymer and a compound in accordance with claim 1.

26. An acrylonitrile-butadiene-styrene copolymer composition having improved resistance to deterioration upon exposure to light comprising an acrylonitrile-butadiene-styrene copolymer and a compound in accordance with claim 1.

* * * * *